US011147643B2

(12) United States Patent
Yoshii et al.

(10) Patent No.: US 11,147,643 B2
(45) Date of Patent: Oct. 19, 2021

(54) MANIPULATOR

(71) Applicant: OLYMPUS CORPORATION, Tokyo (JP)

(72) Inventors: Toshihiro Yoshii, Tokyo (JP); Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 963 days.

(21) Appl. No.: 15/859,981

(22) Filed: Jan. 2, 2018

(65) Prior Publication Data

US 2018/0125595 A1 May 10, 2018

Related U.S. Application Data

(63) Continuation of application No. PCT/JP2016/065963, filed on May 31, 2016.

(30) Foreign Application Priority Data

Jul. 17, 2015 (JP) .............................. JP2015-143123

(51) Int. Cl.
*A61B 34/00* (2016.01)
*B25J 9/10* (2006.01)
(Continued)

(52) U.S. Cl.
CPC .............. *A61B 34/71* (2016.02); *B25J 9/1045* (2013.01); *B25J 17/02* (2013.01); *B25J 18/06* (2013.01);
(Continued)

(58) Field of Classification Search
CPC ......... B25J 9/1045; B25J 9/065; A61B 34/71; A61B 2034/715; F16H 25/183
See application file for complete search history.

(56) References Cited

U.S. PATENT DOCUMENTS 1,751,646 A * 3/1930 Nieman .................... F16C 5/00
74/110
2010/0082041 A1 4/2010 Prisco
(Continued)

FOREIGN PATENT DOCUMENTS

EP 2 517 613 A1 10/2012
EP 3 025 635 A1 6/2016
(Continued)

OTHER PUBLICATIONS

International Search Report dated Aug. 30, 2016 issued in PCT/JP2016/065963.
(Continued)

*Primary Examiner* — Bobby Rushing, Jr.
(74) *Attorney, Agent, or Firm* — Scully, Scott, Murphy & Presser, P.C.

(57) ABSTRACT

Provided is a manipulator including: a movable part; a drive unit generating power; an elongated flexible long guide member to which the part is attached at one end thereof and the drive unit is attached at the other end thereof; an elongated tension transmission member passing through a lumen in the long guide member and transmitting the power of the drive unit to the part by means of a tension; a tension adjusting mechanism adjusting the tension of the tension transmission member; and a holding unit to which the drive unit is detachably attached. The mechanism includes: a tensioner, provided in a movable manner in a direction intersecting the longitudinal direction of the tension transmission member, that pulls the tension transmission member; and a pressing member, provided in the holding unit, that moves the tensioner in a state in which the drive unit has been attached to the holding unit.

6 Claims, 10 Drawing Sheets

(51) Int. Cl.
  *B25J 18/06* (2006.01)
  *B25J 17/02* (2006.01)
  *F16H 25/18* (2006.01)
  *A61B 17/29* (2006.01)
  *A61B 17/00* (2006.01)

(52) U.S. Cl.
  CPC ........ *F16H 25/183* (2013.01); *A61B 17/2909* (2013.01); *A61B 2017/00398* (2013.01); *A61B 2017/2903* (2013.01); *A61B 2017/2915* (2013.01); *A61B 2017/2917* (2013.01); *A61B 2017/2923* (2013.01); *A61B 2017/2927* (2013.01); *A61B 2034/715* (2016.02)

(56) References Cited

U.S. PATENT DOCUMENTS

| | | | |
|---|---|---|---|
| 2012/0046522 | A1 | 2/2012 | Naito |
| 2012/0289973 | A1 | 11/2012 | Prisco et al. |
| 2014/0249545 | A1 | 9/2014 | Hyodo et al. |
| 2016/0135663 | A1 | 5/2016 | Isoda et al. |
| 2016/0166342 | A1 | 6/2016 | Prisco |
| 2016/0310115 | A1 | 10/2016 | Prisco, Sr. et al. |
| 2017/0105805 | A1 | 4/2017 | Hasegawa et al. |
| 2019/0060016 | A1 * | 2/2019 | Hasegawa .............. A61B 34/71 |

FOREIGN PATENT DOCUMENTS

| | | | | |
|---|---|---|---|---|
| EP | 3 168 013 | A1 | 5/2017 | |
| JP | S60074990 | U | 5/1985 | |
| JP | S60172047 | U | 11/1985 | |
| JP | 2002200091 | A | 7/2002 | |
| JP | 2003127076 | A * | 5/2003 | ......... A61B 1/00149 |
| JP | 2010220786 | A | 10/2010 | |
| JP | 2010221329 | A | 10/2010 | |
| JP | 2013103074 | A | 5/2013 | |
| JP | 5542288 | B2 | 7/2014 | |
| JP | 2014159071 | A | 9/2014 | |
| JP | 2015-024007 | A | 2/2015 | |
| JP | 2016-016242 | A | 2/2016 | |
| WO | 2010039387 | A1 | 4/2010 | |
| WO | 2013073713 | A1 | 5/2013 | |
| WO | 2015/012081 | A1 | 1/2015 | |

OTHER PUBLICATIONS

Extended Supplementary European Search Report dated Jan. 18, 2019 in European Patent Application No. 16 82 7507.1.

* cited by examiner

MANIPULATOR

CROSS-REFERENCE TO RELATED APPLICATIONS

This is a continuation of International Application PCT/JP2016/065963 which is hereby incorporated by reference herein in its entirety.

This application is based on Japanese Patent Application No. 2015-143123, the content of which is incorporated herein by reference.

TECHNICAL FIELD

The present invention relates to a manipulator.

BACKGROUND ART

In the related art, there are known surgical instruments using a method in which a curved section or a movable part, such as forceps, disposed at a distal end of a flexible insertion portion is driven by means of a wire (for example, see PTL 1).

The surgical instrument of PTL 1 is provided with a constant-force spring that applies a fixed initial tension to a wire passing through a flexible insertion portion, in order to prevent a fluctuation in the tension of the wire caused when the flexible insertion portion is curved.

CITATION LIST

Patent Literature

{PTL 1} Publication of Japanese Patent No. 5542288

SUMMARY OF INVENTION

According to one aspect, the present invention provides a manipulator including: a movable part; a drive unit that generates power to be supplied to the movable part; an elongated flexible long guide member to which the movable part is attached at one end thereof and the drive unit is attached at the other end thereof; an elongated tension transmission member that passes through a lumen in the long guide member and that transmits the power of the drive unit to the movable part by means of a tension; a tension adjusting mechanism that adjusts the tension of the tension transmission member; and a holding unit to which the drive unit is detachably attached, wherein the tension adjusting mechanism is provided with: a tensioner that is provided in a movable manner in a direction intersecting the longitudinal direction of the tension transmission member and that pulls the tension transmission member; and a pressing member that is provided in the holding unit and that moves the tensioner in a state in which the drive unit has been attached to the holding unit.

DESCRIPTION OF EMBODIMENT

A manipulator 1 according to one embodiment of the present invention will be described below with reference to the drawings.

Figure 1:
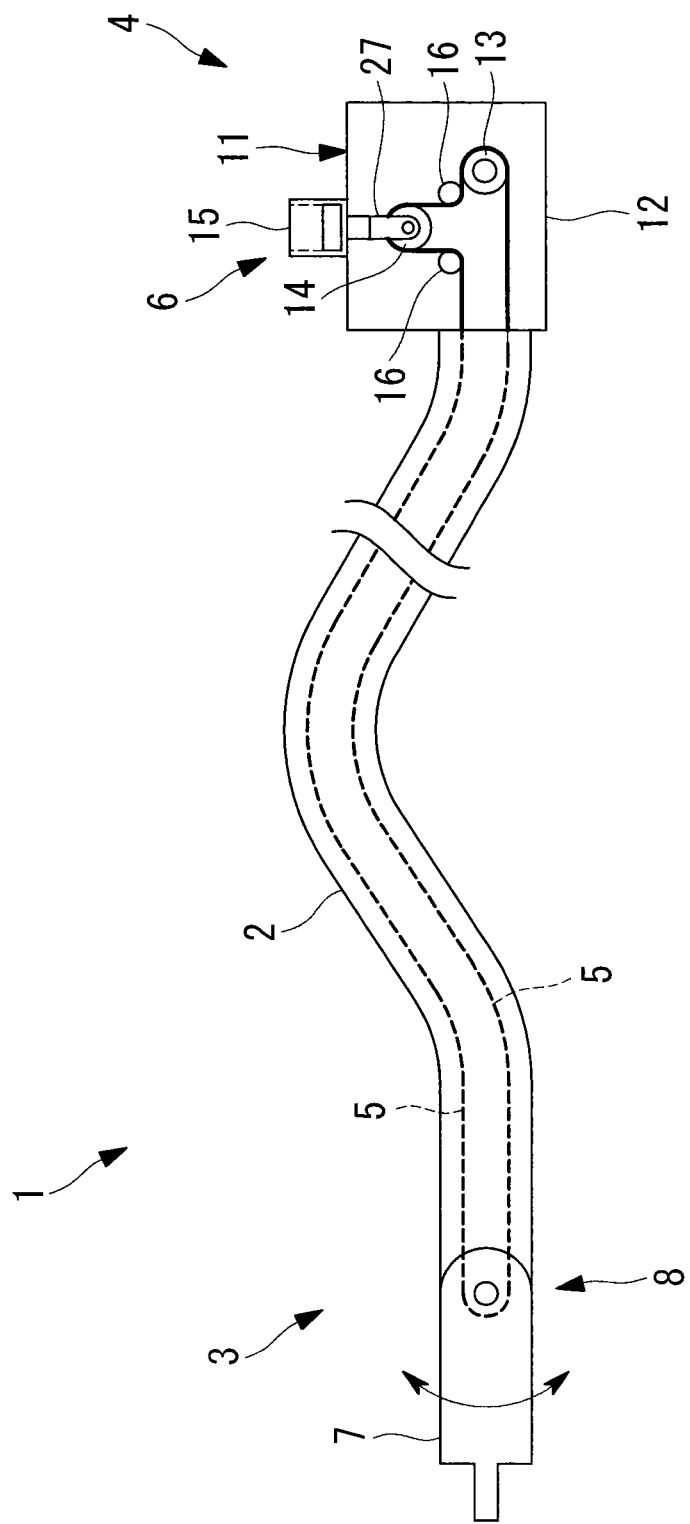
FIG. 1 is a partially cutaway, schematic view showing a manipulator according to one embodiment of the present invention.
Figure 2:
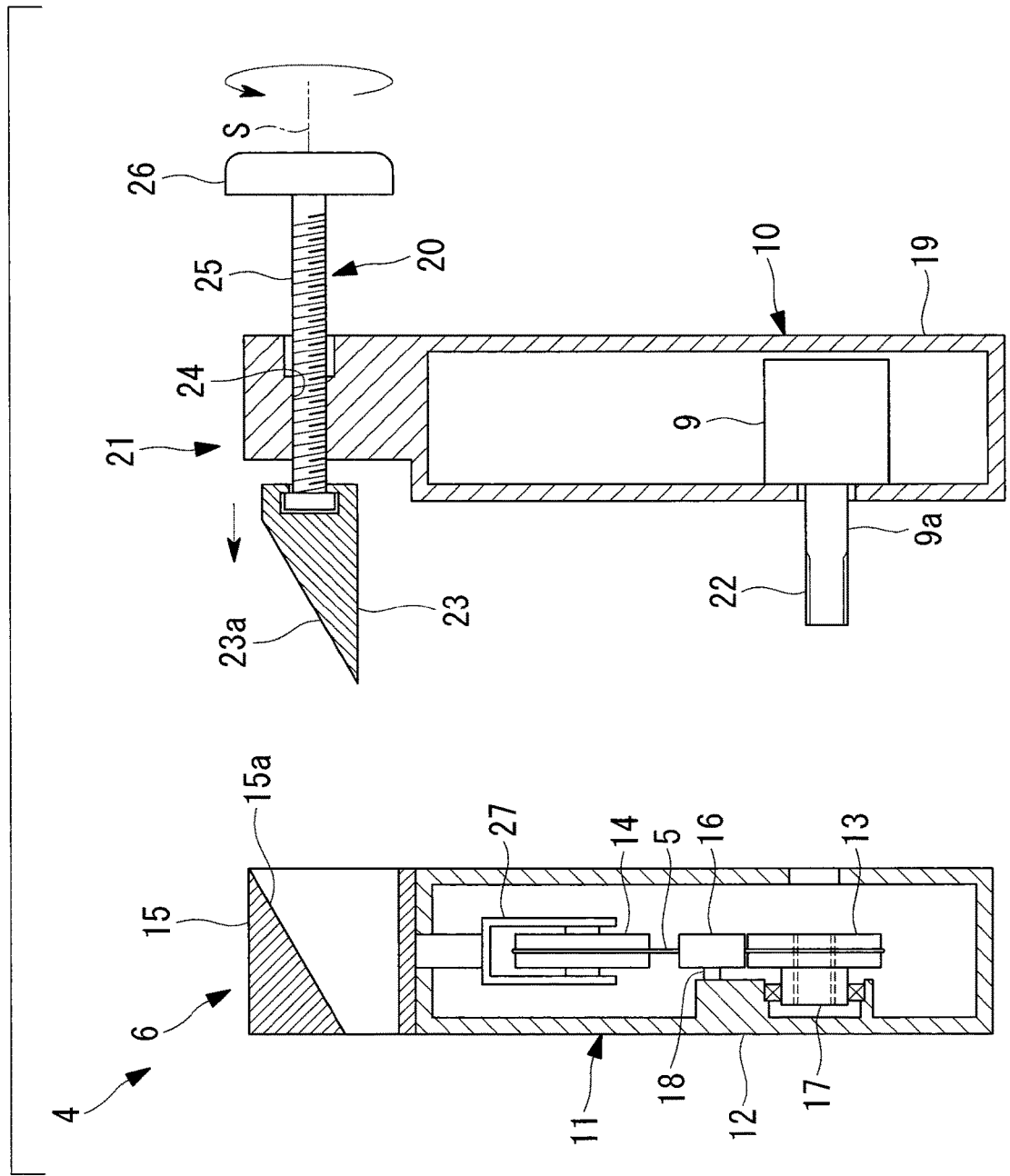
FIG. 2 is a longitudinal sectional view showing a state in which a manipulator-side drive unit and a motor unit that constitute a drive unit of the manipulator shown in FIG. 1 are separated.

As shown in FIGS. 1 and 2, for example, the manipulator 1 of this embodiment is provided with: an elongated flexible long guide member 2 that is inserted into a body cavity of a patient via a channel of an endoscope (not shown) inserted into the body cavity of the patient; a movable part 3 that is disposed at a distal end of the long guide member 2; a drive unit 4 that is disposed at a proximal end of the long guide member 2 and that generates a driving force for operating the movable part 3; a wire (tension transmission member) 5 that transfers, as a tension, the driving force generated by the drive unit 4 to the movable part 3; and a tension adjusting mechanism 6 that adjusts the tension of the wire 5.

The movable part 3 is provided with: a treatment part 7, such as forceps, that acts on an affected area in the body; and at least one joint part 8 that supports the treatment part 7. For ease of explanation, the example shown in the figure shows a case in which the joint part 8 has a single swivel joint for causing the treatment part 7 to swivel about an axis perpendicular to the longitudinal axis of the long guide member 2.

The long guide member 2 is an elongated flexible multi-lumen tube that is provided with a plurality of lumens passing therethrough in the longitudinal direction.

As shown in FIG. 2, the drive unit 4 is provided with: a motor unit (holding unit) 10 that includes a motor 9; and a manipulator-side drive unit 11 that is attached to the proximal end of the multi-lumen tube 2. The motor unit 10 and the manipulator-side drive unit 11 are provided so as to be detachably attached to each other.

The manipulator-side drive unit 11 is provided with: a housing 12 that is fixed to the proximal end of the multi-lumen tube 2; a drive pulley (power converting unit) 13 that is rotatably attached to the housing 12 and around which the wire 5 is looped; a tensioner pulley (tensioner) 14 that pulls a middle section of the wire 5 in a direction perpendicular to the longitudinal direction of the wire 5; and a pulling member 15 that rotatably supports the tensioner pulley 14 and that is supported by the housing 12 in a movable manner in the pulling direction of the wire 5 pulled by the tensioner pulley 14.

In the figure, reference numeral 16 denotes idlers that cause the wire 5 to curve at both sides of the tensioner pulley 14, and reference numeral 17 denotes a bearing that rotatably supports the drive pulley 13 in the housing 12. The respective idlers 16 are provided rotatably about shafts 18 fixed to the housing 12.

As shown in FIG. 2, the pulling member 15 supports the tensioner pulley 14 at one end thereof and is provided with, at the other end thereof, an inclined surface 15a that is inclined with respect to the movement direction of the tensioner pulley 14.

The motor unit 10 is provided with: a housing 19 that is detachably attached to the housing 12 of the manipulator-side drive unit 11; the motor 9, from which a shaft 9a is protruded from the inside of the housing 19 in the attachment direction toward the manipulator-side drive unit 11; and an input unit 21 that inputs the amount of movement of the tensioner pulley 14. A connection part 22, such as a spline gear, for detachably coupling the shaft 9a to the drive pulley 13 is provided at a distal end of the shaft 9a.

The input unit 21 is provided with: a pressing member 23 that has an inclined surface 23a for pressing the inclined surface 15a of the pulling member 15; and a linear motion mechanism 20 that moves the pressing member 23 in the direction parallel to the shaft 9a of the motor 9. In the example shown in the figure, the linear motion mechanism 20 is provided with: a screw hole 24 that is provided in the housing 19; a screw shaft (shaft) 25 that is fastened into the screw hole 24; and a handle 26 that is provided at one end of the screw shaft 25.

The pressing member 23 is attached to the other end of the screw shaft 25 in a rotatable manner about an axis line S of the screw shaft 25. Even when the screw shaft 25 is rotated about the axis line S due to the rotation of the handle 26, the rotational force thereof is not transferred to the pressing member 23, and only the driving force of the screw shaft 25 is transferred to the pressing member 23. Furthermore, the pressing member 23 is provided with a guide (not shown) that suppresses the rotation of the screw shaft 25 about the longitudinal axis thereof.

In order to attach the housing 19 of the motor unit 10 to the housing 12 of the manipulator-side drive unit 11, the inclined surface 23a of the pressing member 23 is located at a position opposed to the inclined surface 15a of the pulling member 15, and movement of the pressing member 23 caused by the actuation of the linear motion mechanism 20 presses the inclined surface 15a and moves the tensioner pulley 14, thus making it possible to increase the tension applied to the wire 5.

Specifically, the tensioner pulley 14, the pulling member 15, and the input unit 21 constitute the tension adjusting mechanism 6, which adjusts the tension of the wire 5.

When the manipulator-side drive unit 11 is coupled to the motor unit 10, the shaft 9a of the motor 9 in the motor unit 10 and the drive pulley 13 in the manipulator-side drive unit 11 are coupled by means of the connection part 22, such as a spline gear. Accordingly, the rotational driving force of the motor 9 is converted into the tension of either side of the wire 5, the tension depending on the rotation direction of the pulleys 13 and 14. Then, the movable part 3 is driven, in the corresponding direction, by means of the tension transferred by the wire 5.

A description will now be given of a case in which treatment is given in the body of a patient by using the thus-configured manipulator 1 of this embodiment.

As shown in FIG. 2, in a state in which the motor unit 10 is detached from the manipulator-side drive unit 11, the manipulator 1 of this embodiment is inserted starting from the movable part 3, which is located at the distal end thereof, via a channel in an insertion portion of an endoscope inserted from outside the body of the patient into a body cavity thereof, and the movable part 3 is made to protrude from an opening of the forceps channel on a distal end surface of the insertion portion of the endoscope, which is now located inside the body.

In this case, the body cavity is mostly tortuous, and the insertion portion of the endoscope and the channel provided in the insertion portion are inserted into the body cavity while being curved conforming to the shape of the body cavity. Therefore, when the manipulator 1 is inserted via such a channel, the manipulator 1 is inserted while causing the long guide member 2 to curve conforming to the channel. Because the motor unit 10, which has a large weight, is detached from the manipulator-side drive unit 11, it is possible to facilitate the insertion work.

In the manipulator 1 of this embodiment, when the long guide member 2 is curved, a lumen formed in the multi-lumen tube, which constitutes the long guide member 2, is also curved, thus increasing the friction with the wire 5 disposed in the lumen.

Thus, as shown in FIG. 2, an operator operates the handle 26 of the input unit 21, which is provided in the motor unit 10, to push out the pressing member 23 by a protrusion amount corresponding to the degree of curvature of the long guide member 2.

Specifically, when the handle 26 is rotated in one direction, the screw shaft 25 is rotated with respect to the screw hole 24, the screw shaft 25 is moved forward by a protrusion amount corresponding to the lead of the screw, and the pressing member 23, which is attached at the distal end of the screw shaft 25, is pushed out.

Figure 3:
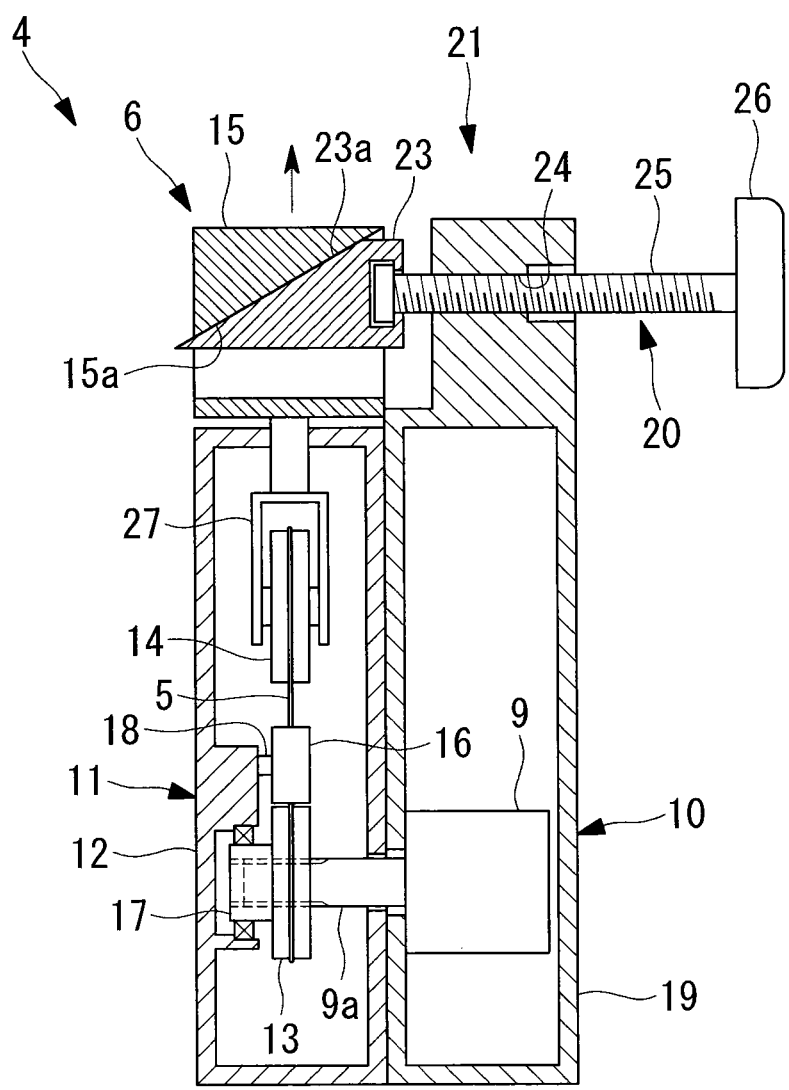
FIG. 3 is a longitudinal sectional view showing a state in which the manipulator-side drive unit and the motor unit shown in FIG. 2 are coupled.

Then, in this state, the housing 12 of the manipulator-side drive unit 11 and the housing 19 of the motor unit 10 are made to come close, thereby coupling the housings 12 and 19 to each other, as shown in FIG. 3.

At this time, the shaft 9a of the motor 9, which protrudes from the motor unit 10, is coupled to the drive pulley 13 in the manipulator-side drive unit 11, so that the rotational force can be transmitted by means of the connection part 22, such as a spline gear. On the other hand, the inclined surface 23a, which is provided on the pressing member 23 of the input unit 21, is brought into close contact with the inclined surface 15a of the pulling member 15 and presses the inclined surface 15a. As a result, the inclined surface 23a of the pressing member 23 presses the inclined surface 15a of the pulling member 15 to move the pulling member 15 until the housings 12 and 19 are completely coupled.

Figure 4:
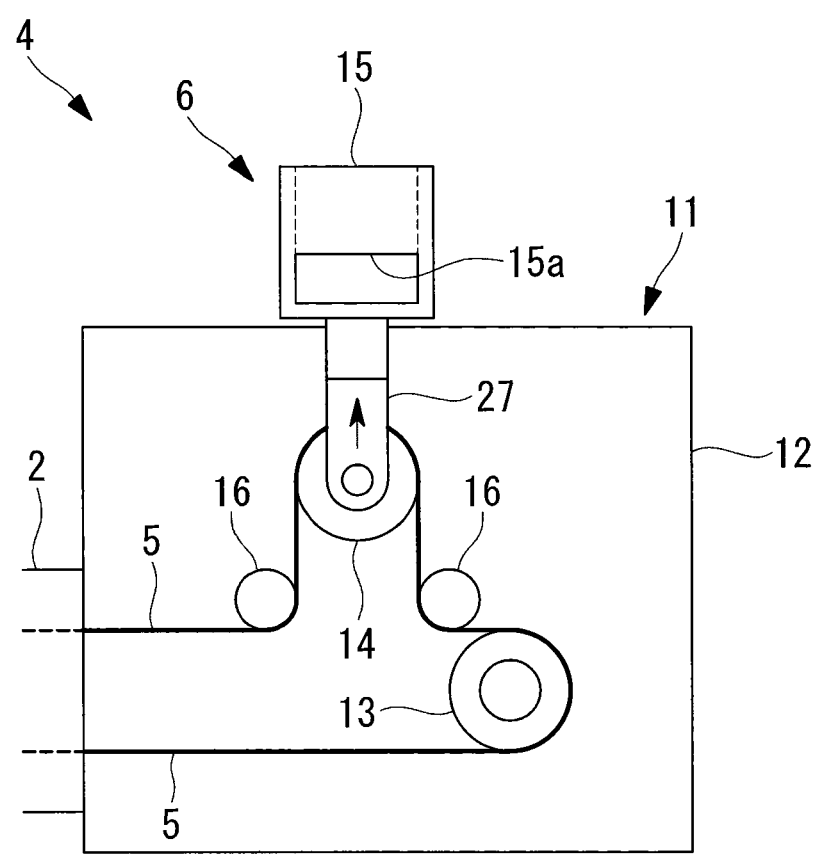
FIG. 4 is a schematic view of the manipulator-side drive unit, for explaining movement of a tensioner pulley in the state shown in FIG. 3.

Specifically, as shown in FIGS. 3 and 4, when the pulling member 15 is moved, the tensioner pulley 14, which is provided at one end of the pulling member 15, is also moved in the same direction. Because the tensioner pulley 14 pulls a middle section of the wire 5 in a direction intersecting the longitudinal direction of the wire 5, the tension applied to the wire 5 is increased according to the amount of movement of the tensioner pulley 14. Accordingly, there is an advantage in that the tensioner pulley 14 is moved by the amount of movement corresponding to the degree of curvature of the long guide member 2, thus making it possible to properly adjust the tension.

Figure 5:
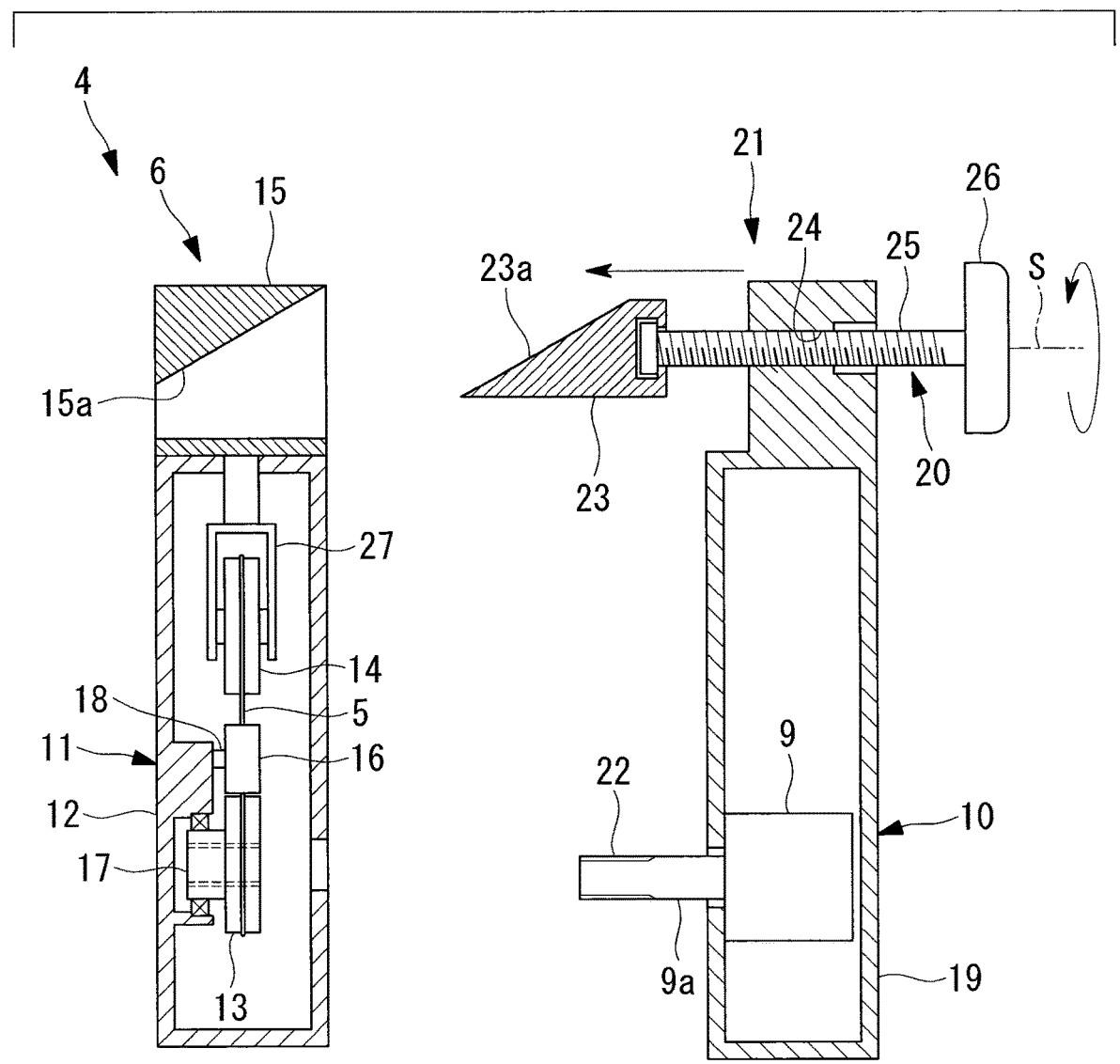
FIG. 5 is a longitudinal sectional view showing a state in which the manipulator-side drive unit and the motor unit are separated, in a case in which a larger tension than that in FIG. 2 is to be applied.
Figure 6:
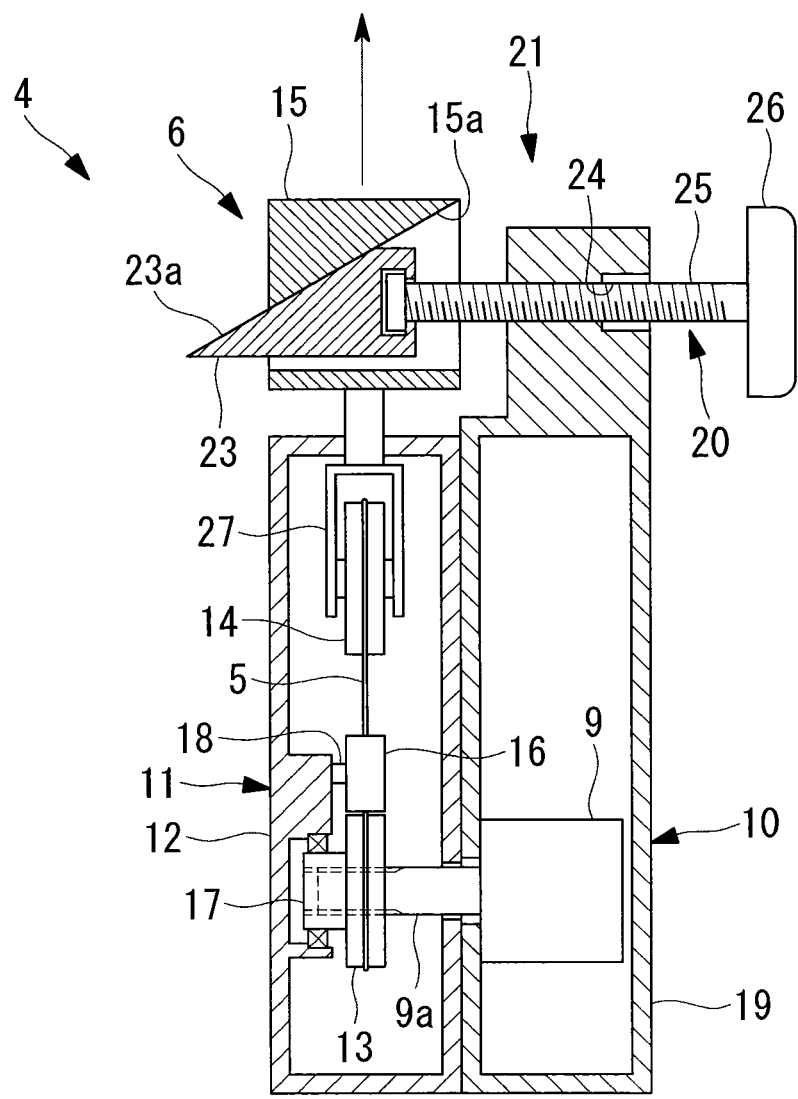
FIG. 6 is a longitudinal sectional view showing a state in which the manipulator-side drive unit and the motor unit shown in FIG. 5 are coupled.
Figure 7:
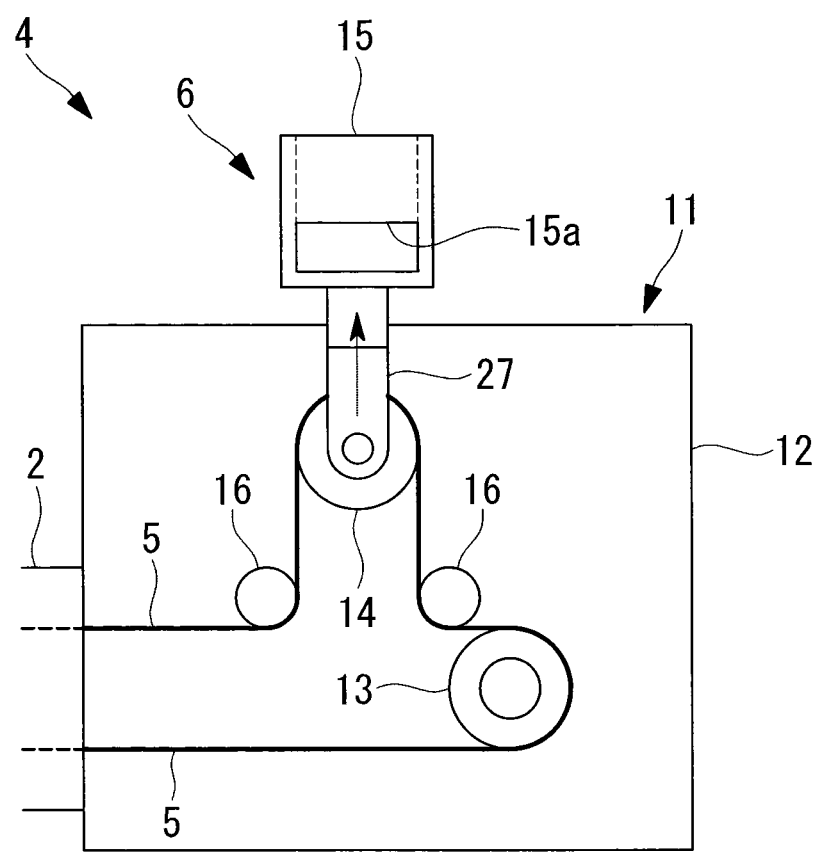
FIG. 7 is a schematic view of the manipulator-side drive unit, for explaining movement of the tensioner pulley in the state shown in FIG. 6.

Furthermore, in order to significantly increase the tension of the wire 5, as shown in FIG. 5, the pressing member 23 is made to significantly protrude through the operation of the handle 26 before both housings 12 and 19 are coupled, and both housings 12 and 19 are coupled to each other, as shown in FIG. 6, thereby making it possible to significantly move the pulling member 15 and to significantly move the tensioner pulley 14, as shown in FIGS. 6 and 7.

Here, the degree of curvature of the long guide member 2, which determines the protrusion amount of the pressing member 23, can be determined by the following method.

Specifically, the degree of curvature of the long guide member 2 may be directly detected by a shape sensor provided on the long guide member 2 or may be externally indirectly detected by an endoscope-insertion-shape measurement device by using a magnetic field or the like. Furthermore, because the curved shape of the long guide member 2 can be estimated depending on the position of an affected area to be treated or the type of the treatment part 7, which is provided in the movable part 3, the protrusion amount may also be determined on the basis of the information thereof.

In this way, according to the manipulator 1 of this embodiment, the pressing member 23 is pushed out to move the tensioner pulley 14, and the motor 9 is coupled to the drive pulley 13, thus making it possible to apply the proper tension to the wire 5, which is an easy operation.

When the long guide member 2 is significantly curved, the tension to be applied to the wire 5 is increased beforehand, thus making it possible to reduce a time delay caused in the operation of the movable part 3 driven by the motor 9, so that there is an advantage in that smooth treatment can be performed.

Note that, in this embodiment, although an example structure in which the pressing member 23 is pushed out through manual operation of the handle 26 is shown as the input unit 21, the input unit 21 is not limited thereto, and it is also possible to adopt a system in which the pressing member 23 is moved by the motor 9 and the linear motion mechanism 20, such as a ball screw.

Furthermore, in this embodiment, although the pressing member 23 is pushed out in advance through operation of the handle 26 before both housings 12 and 19 are coupled, instead of this, it is also possible to push out the pressing member 23 after both housings 12 and 19 are coupled and to adjust the tension of the wire 5.

Furthermore, in this embodiment, although the inclined surface 23a is provided on the pressing member 23, too, and the inclined surface 15a of the pulling member 15 and the inclined surface 23a of the pressing member 23 are brought into close contact with each other, it is also possible to provide an inclined surface on one of them. In this case, it is preferred that the other of them be provided with rollers that roll on the inclined surface.

Furthermore, in this embodiment, although the tension of the wire 5 is adjusted when the manipulator-side drive unit 11, which does not include the motor 9, is attached to the motor unit 10, which includes the motor 9, instead of this, the manipulator-side drive unit 11 may include the motor 9 coupled to the drive pulley 13. In this case, it is also possible to adopt a slider that fixes the manipulator-side drive unit 11 in order to move the whole manipulator 1 or a holding unit, such as a fixed base, that fixes the manipulator-side drive unit 11 during a surgical operation.

Figure 8:
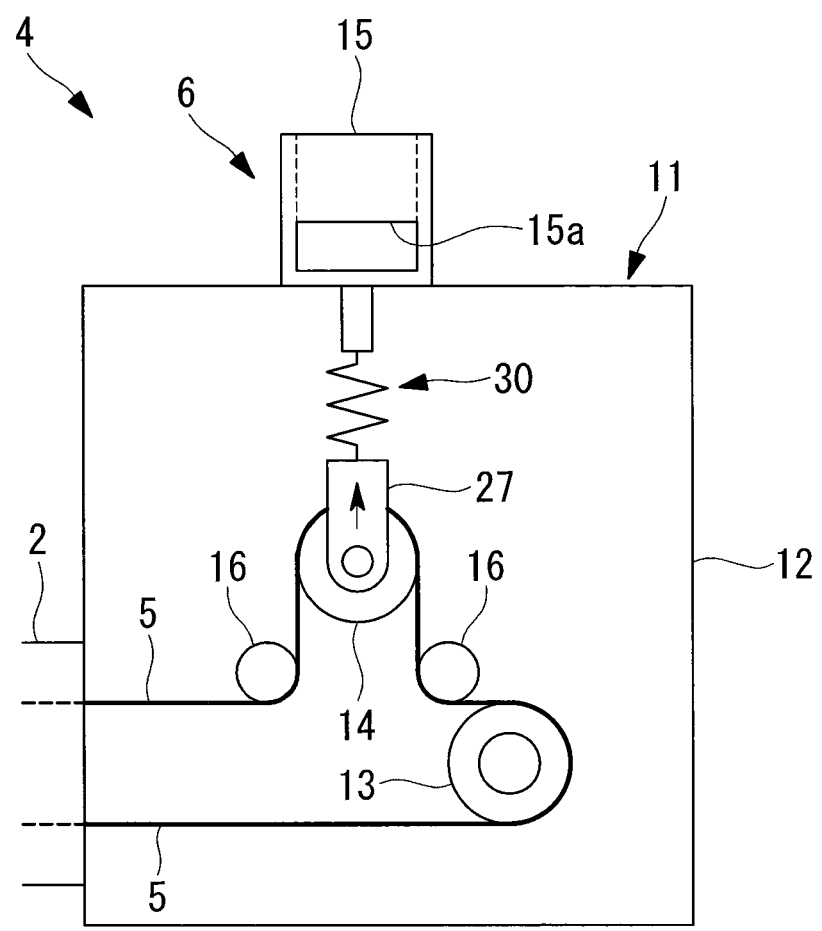
FIG. 8 is a schematic view showing a manipulator-side drive unit in a modification of the manipulator shown in FIG. 1.

Furthermore, in this embodiment, as shown in FIG. 8, it is also possible to dispose, between the tensioner pulley 14 and the pulling member 15, a tension spring (elastic member) 30 that constantly biases the tensioner pulley 14 in the direction in which the tensioner pulley 14 is attracted toward the pulling member 15. By doing so, because a tension is constantly applied to the wire 5 by the biasing force of the tension spring 30, it is possible to prevent looseness of the wire 5 in a state in which the motor unit 10 has not yet been coupled to the manipulator-side drive unit 11.

Figure 9:
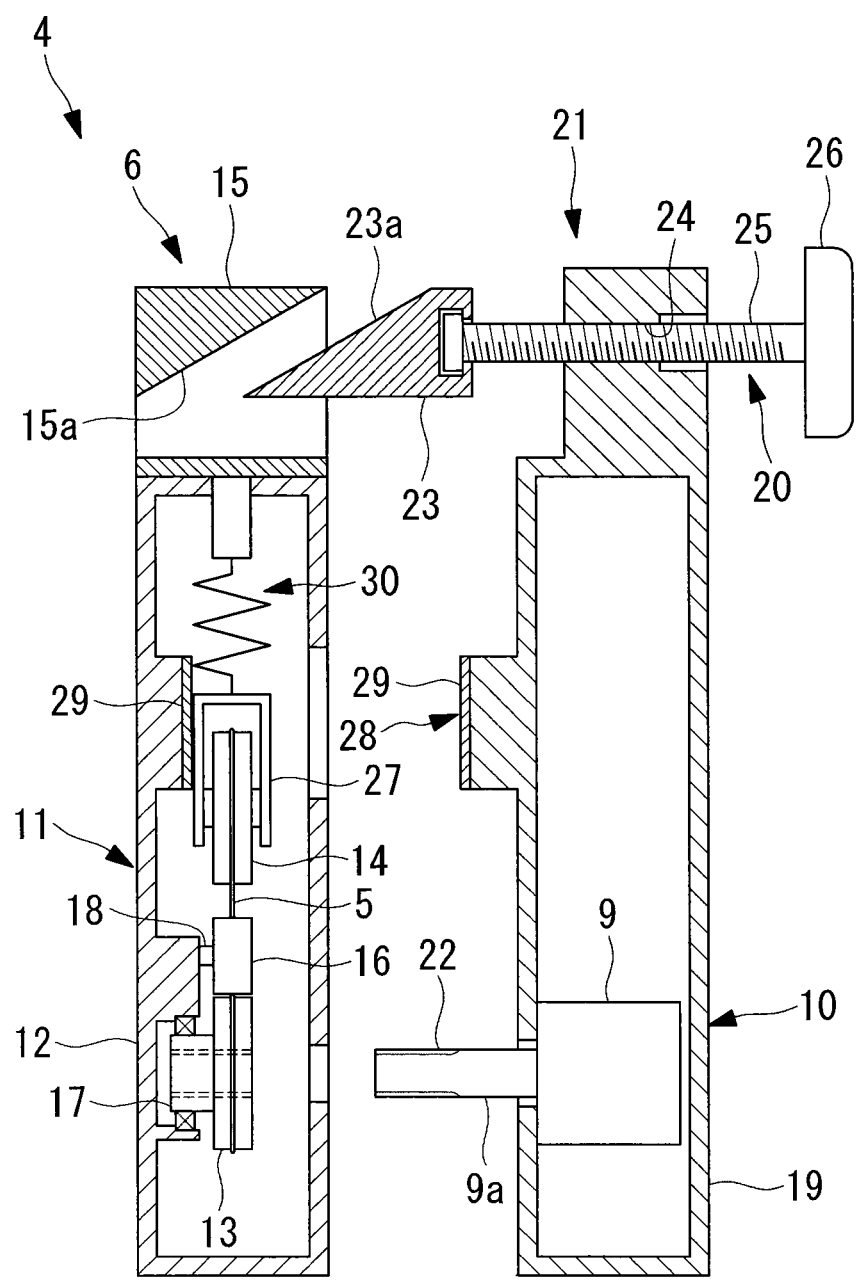
FIG. 9 is a longitudinal sectional view showing a state in which the manipulator-side drive unit and a motor unit that constitute a drive unit of a manipulator shown in FIG. 8 are separated.
Figure 10:
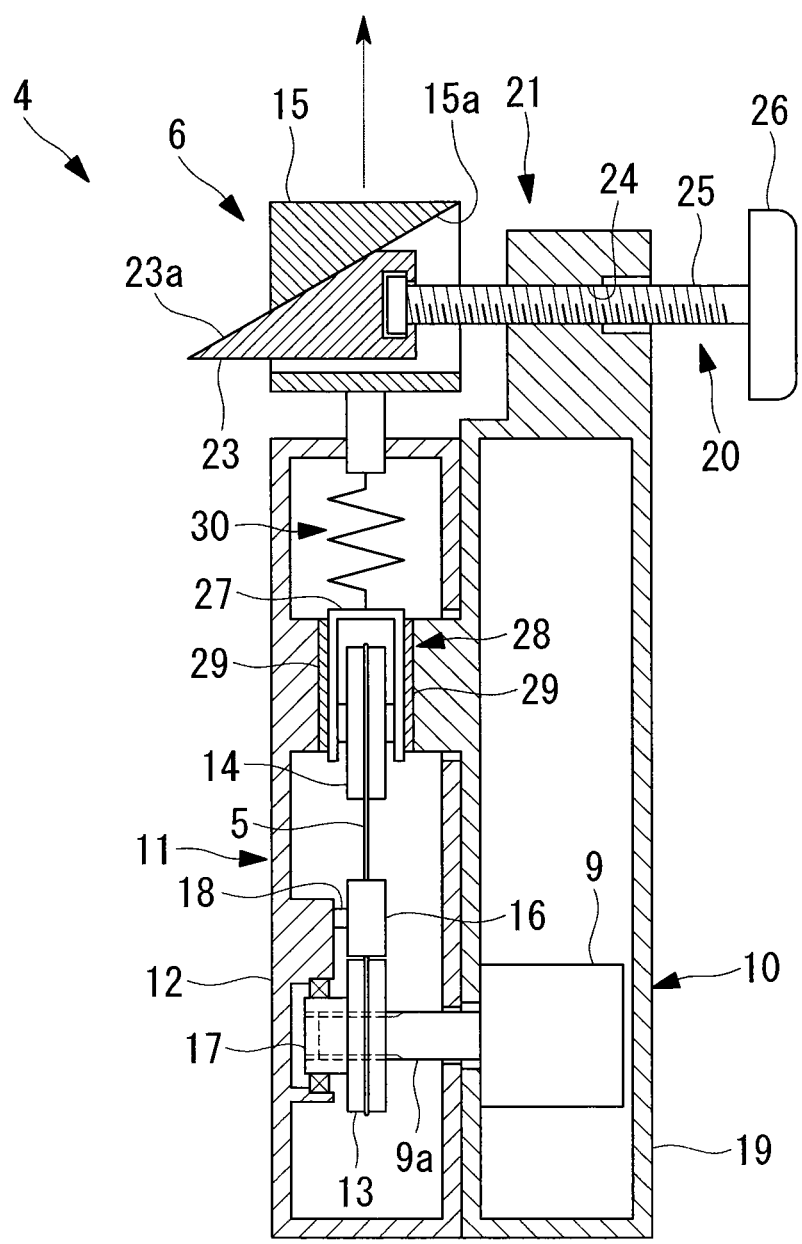
FIG. 10 is a longitudinal sectional view showing a state in which the manipulator-side drive unit and the motor unit shown in FIG. 9 are coupled.

Then, in this case, it is preferable to provide a pulley fixing mechanism 28 that is provided, at positions so as to sandwich a bracket 27 to which the tensioner pulley 14 is rotatably attached, on an inner surface of the housing 12 of the manipulator-side drive unit 11 and on an external surface of the housing 19 of the motor unit 10, as shown in FIG. 9, and that fixes the tensioner pulley 14 with the bracket 27 sandwiched therebetween, in a state in which the both housings 12 and 19 have been coupled, as shown in FIG. 10. In the figure, reference numeral 29 denotes friction increasing members, such as rubber plates, that are brought into close contact with the bracket 27 to hold the bracket 27 so as to prevent the bracket 27 from being moved, due to large friction forces thereof.

After the proper tension is applied to the wire 5, the tensioner pulley 14 is fixed, thereby making it possible to suppress a fluctuation in the tension of the wire 5 while the movable part 3 is being operated.

Furthermore, in this embodiment, the input unit 21 may be provided with a pressure sensor (sensor, not shown) that detects a pressing force applied to the screw shaft 25. It is preferred that the pressure sensor be provided at a position closer to the pressing member 23 than the screw hole 24 is.

Accordingly, in a state in which the shaft 9a has been coupled to the drive pulley 13, when the motor 9 in the motor unit 10 is actuated, and the pressing member 23 is pushed in, the pressing force detected by the pressure sensor, which is provided for the screw shaft 25, is increased; thus, the operation of the tension adjusting mechanism 6 is stopped at the point in time the pressing force reaches a predetermined pressure, thereby making it possible to properly adjust the tension of the wire 5.

The above-described embodiment leads to the following invention.

According to one aspect, the present invention provides a manipulator including: a movable part; a drive unit that generates power to be supplied to the movable part; an elongated flexible long guide member to which the movable part is attached at one end thereof and the drive unit is attached at the other end thereof; an elongated tension transmission member that passes through a lumen in the long guide member and that transmits the power of the drive unit to the movable part by means of a tension; a tension adjusting mechanism that adjusts the tension of the tension transmission member; and a holding unit to which the drive unit is detachably attached, wherein the tension adjusting mechanism is provided with: a tensioner that is provided in a movable manner in a direction intersecting the longitudinal direction of the tension transmission member and that pulls the tension transmission member; and a pressing member that is provided in the holding unit and that moves the tensioner in a state in which the drive unit has been attached to the holding unit.

According to this aspect, power generated in the drive unit through actuation of the drive unit is transferred to the movable part via the tension transmission member by means of a tension, thus operating the movable part. When the long guide member is curved, the lumen in the long guide member is also curved; therefore, the tension transmission member is guided in the curved lumen, to transfer the tension.

In this case, when the long guide member is considerably curved, the friction between the tension transmission member and the lumen is increased; thus, it is difficult to transfer the power to the movable part unless a large tension is applied.

According to this aspect, in a state in which the drive unit has been attached to the holding unit, the pressing member, which is provided in the holding unit, moves the tensioner in a direction intersecting the longitudinal direction of the tension transmission member, thereby pulling the tension transmission member by means of the tensioner and making it possible to increase the tension applied to the tension transmission member. The amount of movement of the tensioner moved by the pressing member is adjusted, thereby making it possible to apply the proper tension to the tension transmission member according to the shape of the long guide member and to smoothly operate the curved section or the movable part, such as forceps.

In the above-described aspect, the holding unit may be provided with a motor; and the drive unit may be provided with a power converting unit that is connected to the motor when the drive unit is attached to the holding unit and that converts a rotational force of the motor into a tension of the tension transmission member.

By doing so, in a state in which the drive unit has not yet been attached to the holding unit, the long guide member is inserted into the body cavity while being curved, and the drive unit is attached to the holding unit in a state in which the movable part is disposed in the vicinity of an affected area, thus connecting the motor, which is provided in the holding unit, and the power converting unit, which is provided in the drive unit.

Accordingly, when the motor is actuated, a rotational force of the motor is converted into a tension to be applied to the tension transmission member by the power converting unit, and the tension is transferred to the movable part by the tension transmission member, thus operating the movable part. Through an operation for attaching the drive unit to the holding unit in order to connect the motor to the drive unit, it is possible to apply the proper tension to the tension transmission member and to smoothly operate the curved section or the movable part, such as forceps.

Furthermore, in the above-described aspect, the tension adjusting mechanism may be provided with a pulling member that is connected to the tensioner and that is supported in a movable manner in the movement direction of the tensioner; the pressing member may be moved in a direction intersecting the movement direction of the pulling member; and at least one of the pressing member and the pulling member may be provided with an inclined surface that converts movement of the pressing member into movement of the pulling member.

By doing so, the direction in which the motor, which is provided in the holding unit, is connected to the power converting unit is merely matched, in advance, to the movement direction of the pressing member, thereby bringing the drive unit and the holding unit close to each other in one direction, and, through an operation for attaching the drive unit to the holding unit, it is possible to convert movement of the pressing member into movement of the pulling member by means of the inclined surface and to increase a tension to be applied to the tension transmission member by the tensioner, which is connected to the pulling member. Specifically, with a simple operation, it is possible to apply the proper tension to the tension transmission member and to smoothly operate the curved section or the movable part, such as forceps.

Furthermore, the above-described aspect may further include, between the tensioner and the pulling member, an elastic member that constantly biases the tensioner in the direction in which the tensioner is attracted toward the pulling member.

By doing so, even in a state in which the motor and the power converting unit have not yet been connected, the tensioner is pulled toward the pulling member by the biasing force of the elastic member, which is provided between the pulling member and the tensioner. Therefore, the fixed tension is applied to the tension transmission member by the tensioner, thus preventing looseness of the tension transmission member. When the drive unit is attached to the holding unit, the pulling member is moved, thereby making it possible to increase the biasing force caused by the elastic member, to increase the tension applied to the tension transmission member, to apply the proper tension to the tension transmission member, and to smoothly operate the curved section or the movable part, such as forceps.

Furthermore, in the above-described aspect, the tension adjusting mechanism may be provided with a sensor that detects a pressing force applied from the pulling member to the pressing member.

By doing so, movement of the tensioner caused by the tension adjusting mechanism can be constrained at a position where the proper tension is applied to the tension transmission member, on the basis of the detected pressing force.

Furthermore, in the above-described aspect, the tension adjusting mechanism may be provided with a shaft that presses the pressing member; and the sensor may be a pressure sensor that detects the pressing force caused in the shaft.

REFERENCE SIGNS LIST 1 manipulator
2 long guide member
3 movable part
4 drive unit
5 wire (tension transmission member)
6 tension adjusting mechanism
9 motor
10 motor unit (holding unit)
13 drive pulley (power converting unit)
14 tensioner pulley (tensioner)
15 pulling member
15a inclined surface
23 pressing member
23a inclined surface
25 screw shaft (shaft)
30 tension spring (elastic member)

The invention claimed is:
1. A manipulator comprising:
an elongated flexible member;
a movable part disposed on a distal end of the elongated flexible member;
a first housing disposed on a proximal end of the elongated flexible member;
a second housing detachably attached to the first housing, the second housing including an actuator configured to generate power to be supplied to the movable part;

a wire that passes through the elongated flexible member, the wire being configured to transmit the power of the actuator to the movable part when the second housing has been attached to the first housing; and a tension adjusting mechanism configured to adjust a tension of the wire, wherein the tension adjusting mechanism comprises:
- a tensioner disposed on the first housing, the tensioner being configured to increase the tension of the wire by being moved in a direction intersecting the longitudinal direction of the wire;
- a pulling member disposed on the first housing, the pulling member being configured to support and pull the tensioner; and
- a pressing member disposed on the second housing, the pressing member being configured to press the pulling member when the second housing has been attached to the first housing, wherein the pressing member is moved in a direction intersecting the movement direction of the pulling member, and wherein at least one of the pressing member and the pulling member is provided with an inclined surface that converts linear movement of the pressing member into linear movement of the pulling member.

2. The manipulator according to claim 1,
wherein the actuator is a motor; and
the first housing has a pulley around which the wire is wound, the pulley being configured to convert a rotational force of the motor into a tension of the wire when the second housing has been attached to the first housing.

3. The manipulator according to claim 1, further comprising, an elastic member disposed between the tensioner and the pulling member, the elastic member being configured to constantly bias the tensioner in the direction in which the tensioner is attracted toward the pulling member.

4. The manipulator according to claim 1, wherein the tension adjusting mechanism further comprises a sensor configured to detect a pressing force applied from the pulling member to the pressing member.

5. The manipulator according to claim 4,
wherein the tension adjusting mechanism further comprises a shaft configure to press the pressing member; and
the sensor is configured to detect the pressing force caused in the shaft.

6. The manipulator according to claim 1, wherein the tension adjusting mechanism further comprises a handle configured to adjust the tension of the wire by moving the pulling member via the pressing member.

* * * * *